United States Patent
Cooper et al.

(10) Patent No.: US 8,256,319 B2
(45) Date of Patent: *Sep. 4, 2012

(54) OFFSET REMOTE CENTER MANIPULATOR FOR ROBOTIC SURGERY

(75) Inventors: Thomas G. Cooper, Menlo Park, CA (US); Todd R. Solomon, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/251,881

(22) Filed: Oct. 3, 2011

(65) Prior Publication Data

US 2012/0083802 A1 Apr. 5, 2012

Related U.S. Application Data

(63) Continuation of application No. 12/499,392, filed on Jul. 8, 2009, now Pat. No. 8,062,288, which is a continuation of application No. 10/957,077, filed on Sep. 30, 2004, now Pat. No. 7,594,912.

(51) Int. Cl.
*A61B 17/00* (2006.01)

(52) U.S. Cl. ......... 74/490.01; 606/1; 606/130; 600/102; 901/41

(58) Field of Classification Search .................. None
See application file for complete search history.

(56) References Cited

U.S. PATENT DOCUMENTS

| | | | |
|---|---|---|---|
| 2,815,697 A | 12/1957 | Saunders-Singer | |
| 3,463,329 A | 8/1969 | Gartner | |
| 4,260,319 A | 4/1981 | Motoda et al. | |
| 4,543,033 A | 9/1985 | Czermak et al. | |
| 4,696,501 A | 9/1987 | Webb | |
| 4,897,015 A | 1/1990 | Abbe et al. | |
| 4,921,393 A | 5/1990 | Andeen et al. | |
| 5,060,532 A | 10/1991 | Barker | |
| 5,078,140 A | 1/1992 | Kwoh | |
| 5,129,911 A | 7/1992 | Siczek et al. | |
| 5,184,601 A | 2/1993 | Putman | |
| 5,209,747 A | 5/1993 | Knoepfler | |
| 5,217,003 A | 6/1993 | Wilk | |
| 5,217,453 A | 6/1993 | Wilk | |
| 5,219,351 A | 6/1993 | Teubner et al. | |
| 5,222,409 A | 6/1993 | Dalakian | |
| 5,257,998 A | 11/1993 | Ota et al. | |
| 5,273,039 A | 12/1993 | Fujiwara et al. | |

(Continued)

FOREIGN PATENT DOCUMENTS

CH 482439 12/1969

(Continued)

OTHER PUBLICATIONS

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1973, pp. 121-136, vol. 2, Springer-Verlag.

(Continued)

*Primary Examiner* — Sam Yao
*Assistant Examiner* — Lynsey Crandall

(57) ABSTRACT

Medical, surgical, and/or robotic devices and systems often including offset remote center parallelogram manipulator linkage assemblies which constrains a position of a surgical instrument during minimally invasive robotic surgery are disclosed. The improved remote center manipulator linkage assembly advantageously enhances the range of instrument motion while at the same time reduces the overall complexity, size, and physical weight of the robotic surgical system.

10 Claims, 13 Drawing Sheets

U.S. PATENT DOCUMENTS

| | | | |
|---|---|---|---|
| 5,279,309 A | 1/1994 | Taylor et al. |
| 5,339,799 A | 8/1994 | Kami et al. |
| 5,343,385 A | 8/1994 | Joskowicz et al. |
| 5,368,015 A | 11/1994 | Wilk |
| 5,397,323 A | 3/1995 | Taylor et al. |
| 5,402,801 A | 4/1995 | Taylor |
| 5,417,210 A | 5/1995 | Funda et al. |
| 5,445,166 A | 8/1995 | Taylor |
| 5,572,999 A | 11/1996 | Funda et al. |
| 5,630,431 A | 5/1997 | Taylor |
| 5,695,500 A | 12/1997 | Taylor et al. |
| 5,697,939 A | 12/1997 | Kubota et al. |
| 5,749,362 A | 5/1998 | Funda et al. |
| 5,762,458 A | 6/1998 | Wang et al. |
| 5,792,135 A | 8/1998 | Madhani et al. |
| 5,800,423 A | 9/1998 | Jensen |
| 5,808,665 A | 9/1998 | Green |
| 5,815,640 A | 9/1998 | Wang et al. |
| 5,817,084 A | 10/1998 | Jensen |
| 5,841,950 A | 11/1998 | Wang et al. |
| 5,855,583 A | 1/1999 | Wang et al. |
| 5,876,325 A | 3/1999 | Mizuno et al. |
| 5,878,193 A | 3/1999 | Wang et al. |
| 5,907,664 A | 5/1999 | Wang et al. |
| 5,931,832 A | 8/1999 | Jensen |
| 6,001,108 A | 12/1999 | Wang et al. |
| 6,007,550 A | 12/1999 | Wang et al. |
| 6,106,511 A | 8/2000 | Jensen |
| 6,246,200 B1 | 6/2001 | Blumenkranz et al. |
| 6,346,072 B1 | 2/2002 | Cooper |
| 6,406,472 B1 | 6/2002 | Jensen |
| 6,441,577 B2 | 8/2002 | Blumenkranz et al. |
| 6,451,027 B1 | 9/2002 | Cooper et al. |
| 6,594,552 B1 | 7/2003 | Nowlin et al. |
| 6,676,669 B2 | 1/2004 | Charles et al. |
| 6,702,805 B1 | 3/2004 | Stuart |
| 6,758,843 B2 | 7/2004 | Jensen |
| 6,788,018 B1 | 9/2004 | Blumenkranz |
| 7,108,688 B2 | 9/2006 | Jensen |
| 2005/0043718 A1 | 2/2005 | Madhani et al. |
| 2007/0089557 A1 | 4/2007 | Solomon et al. |

FOREIGN PATENT DOCUMENTS

| | | |
|---|---|---|
| DE | 2819976 | 11/1979 |
| EP | 239409 | 9/1987 |
| EP | 0291292 | 11/1988 |
| EP | 0595291 | 5/1994 |
| FR | 2460762 | 1/1981 |
| FR | 2593106 | 3/1990 |
| FR | 2845889 | 2/2005 |
| GB | 2117732 | 10/1983 |
| JP | 7059788 A2 | 3/1995 |
| JP | 7136173 A2 | 5/1995 |
| WO | WO9501757 | 1/1995 |

OTHER PUBLICATIONS

Ben Gayed, M. et al., "An Advanced Control Micromanipulator for Surgical Applications," Systems Science, 1987, pp. 123-134, vol. 13.

Guerrouad, Aicha et al., "SMOS: Stereotaxical Microtelemanipulator for Ocular Surgery," IEEE Engineering in Medicine & Biology Society 11th annual international conference, Nov. 9-12, 1989, pp. 879-880, vol. 3, IEEE.

Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.

PCT/US05/32488 International Search Report, mailed May 9, 2006, 4 pages.

PCT/US05/32488 Written Opinion of the International Search Authority, received May 10, 2006, 7 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

OFFSET REMOTE CENTER MANIPULATOR FOR ROBOTIC SURGERY

CROSS REFERENCE TO RELATED APPLICATION

This application is a continuation of application Ser. No. 12/499,392 filed Jul. 9, 2009 which is a continuation of Ser. No. 10/957,077, filed Sep. 30, 2004, the full disclosure of which is incorporated herein by reference.

BACKGROUND OF THE INVENTION

The present invention is generally related to medical, surgical, and/or robotic devices and systems. In an exemplary embodiment, the invention provides offset remote center manipulators which constrain a position of a surgical instrument during minimally invasive robotic surgery.

Minimally invasive medical techniques are intended to reduce the amount of extraneous tissue which is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor which relays input commands from the master controllers to the associated robotic arm and instrument assemblies and back from the instrument and arm assemblies to the associated master controllers in the case of e.g., force feedback or the like. One example of a robotic surgical system is the DA VINCI® system available from Intuitive Surgical, Inc. of Mountain View, Calif.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 6,758, 843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument pivots about a center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing dangerous forces against the abdominal wall. Alternative manipulator structures are described, for example, in U.S. Pat. Nos. 6,702,805; 6,676,669; 5,855,583; 5,808,665; 5,445, 166; and 5,184,601, the full disclosures of which are incorporated herein by reference.

While the new telesurgical systems and device have proven highly effective and advantageous, still further improvements would be desirable. In general, it would be desirable to provide improved structures and systems for performing minimally invasive robotic surgery. More specifically, it would be beneficial to enhance the efficiency and ease of use of these systems. For example, it would be particularly beneficial to improve the range of motion provided by the robotic surgical manipulator while at the same time reducing the overall complexity, size, and physical weight of the system.

BRIEF SUMMARY OF THE INVENTION

The present invention is generally related to medical, surgical, and/or robotic devices and systems. In particular, the present invention is directed to improved remote center manipulators used to support a surgical instrument and provide a center of spherical rotation, remote from any bearings or mechanical supports, at a desired location of the instrument during minimally invasive robotic surgery. The remote center manipulator constrains the instrument to move around a fixed center of rotation, which is preferably coincident with an entry incision in a patient, such as the patient's abdominal wall. In an exemplary embodiment, the invention provides an offset remote center parallelogram manipulator linkage assembly which constrains a position of a surgical instrument during minimally invasive robotic surgery. The improved remote center manipulator advantageously enhances the range of instrument motion along first and second axes while at the same time reduces the overall complexity, size, and physical weight of the robotic surgical system. Such advantages in turn enhance the efficiency and ease of use of such robotic surgical systems.

In a first aspect of the present invention, a remote center manipulator for constraining a position of a surgical instrument is provided. The surgical instrument coupleable to an instrument holder during minimally invasive robotic surgery includes an elongate shaft. The shaft has a distal working end configured for insertion through an incision in a body wall into a body cavity of a patient. The remote center manipulator comprises an articulate linkage assembly having a mounting base rotationally coupled to a parallelogram linkage base for rotation about a first axis. The parallelogram linkage base is coupled to the instrument holder by a plurality of links and joints. The links and joints define a parallelogram so as to constrain the elongate shaft of the instrument relative to a center of rotation when the instrument is mounted to the instrument holder and the shaft is moved in at least one degree of freedom. The first axis and a first side of the parallelogram adjacent the parallelogram linkage base intersect the shaft at the center of rotation. Significantly, the first side of the parallelogram is angularly offset from the first axis.

The first side of the parallelogram is angularly offset from the first axis by at least 2 degrees, preferably by 10 degrees. Generally, the first side of the parallelogram is angularly offset from the first axis in a range from about 2 degrees to about 45 degrees, preferably in a range from about 2 degrees to about 35 degrees. The first side of the parallelogram may sometimes extend beneath the first axis, generally at least one side of the parallelogram extends beneath the first axis. The manipulator provides an improved range of shaft motion that is greater than ±90 degrees along the first axis, preferably greater than ±95 degrees along the first axis. In particular, the cantilevered parallelogram linkage base provides shaft motion in a range from ±168 degrees along the first axis, wherein the first axis is sometimes referred to as a yaw axis. Advantageously, the offset articulate linkage assembly provides an improved range of shaft motion that is greater than ±55 degrees along a second axis, preferably greater than ±60 degrees along the second axis. Generally, the offset articulate linkage assembly provides improved shaft motion in a range from ±75 degrees along the second axis, wherein the second axis is sometimes referred to as a pitch axis.

Preferably, at least one of the links is bent at an angle so as to provide clearance for another link to rest on the bent link. This clearance prevents inter-linkage collisions so as to further allow for an improved range of pitch motion. For example, the link may be bent at an angle of about 22 degrees. The manipulator may not be balanced in at least one degree of freedom. As such, a brake system may be coupled to the articulate linkage assembly. The brake system releasably inhibits articulation of at least one of the joints. Preferably, the plurality of links and joints comprise at least one pulley and at least one flexible element coupled to the pulley that is configured to constrain shaft motion relative to the center of rotation. In one embodiment, the plurality of links and joints comprise a linkage having six pulleys and four belts. The plurality of links and joints are driven by a servomechanism. The plurality of links and the parallelogram linkage base may be offset in different planes so as to reduce the possibility of inter-linkage collisions. The plurality of links and the instrument holder however may be located in the same plane.

In general, the articulate linkage assembly is configured to constrain shaft motion relative to the center of rotation. As such, the shaft is maintained substantially aligned through the center of rotation as the shaft is pivotally moved in at least one degree of freedom. Preferably, the center of rotation is aligned with the incision point to the internal surgical site, for example, with a trocar or cannula at an abdominal wall during laparoscopic surgery. As such, an end effector of the surgical instrument can be positioned safely by moving the proximal end of the shaft using the offset remote center robotic manipulator without imposing dangerous forces against the abdominal wall.

In another aspect of the present invention, a remote center manipulator for constraining a position of a surgical instrument is provided. The surgical instrument coupleable to an instrument holder during minimally invasive robotic surgery includes an elongate shaft. The shaft has a distal working end configured for insertion through an incision in a body wall into a body cavity of a patient. The remote center manipulator comprises an articulate linkage assembly having a mounting base rotationally coupled to a parallelogram linkage base for rotation about a first axis. The parallelogram linkage base is coupled to the instrument holder by a plurality of links and pivots. The links and pivots define a parallelogram so as to constrain the elongate shaft of the instrument relative to a center of rotation when the instrument is mounted to the instrument holder and the shaft is moved along a plane of the parallelogram. Significantly, the first axis and a first pivot of the parallelogram adjacent the parallelogram linkage base are angularly offset and at least one of the links is bent.

The first pivot of the parallelogram is angularly offset from the first axis by at least 2 degrees, preferably by 10 degrees. Generally, the first pivot of the parallelogram is angularly offset from the first axis in a range from about 2 degrees to about 45 degrees, preferably in a range from about 2 degrees to about 35 degrees. The first pivot of the parallelogram may sometimes extend beneath the first axis, generally at least one pivot of the parallelogram extends beneath the first axis. The manipulator provides shaft motion in a range greater than ±90 degrees along the first axis, preferably greater than ±95 degrees along the first axis. In particular, the cantilevered parallelogram linkage base provides improved shaft motion in a range from ±168 degrees along the first axis, e.g., yaw axis. Advantageously, the offset parallelogram and bent link together provide shaft motion in a range greater than ±55 degrees along a second axis, preferably greater than ±60 degrees along the second axis. Typically, the offset parallelogram and bent link provide improved shaft motion in a range from ±75 degrees along the second axis, e.g., pitch axis.

At least one link is bent at an angle (e.g., 22 degrees) so as to provide clearance for another link to rest on the bent link. At least one of the links and pivots are not balanced in at least one degree of freedom. Accordingly, a brake system is coupled to the articulate linkage assembly, the brake system releasably inhibiting articulation of at least one of the pivots. Preferably, the plurality of links and pivots comprise at least one pulley and at least one flexible element coupled to the pulley that is configured to constrain shaft motion relative to the center of rotation. In one embodiment, the plurality of links and pivots comprise a linkage having six pulleys and four belts. The plurality of links and the parallelogram linkage base may be offset in different planes, while the plurality of links and the instrument holder however may be located in the same plane.

In yet another aspect of the present invention, a remote center manipulator for constraining a position of a surgical instrument is provided. The surgical instrument coupleable to an instrument holder during minimally invasive robotic surgery includes an elongate shaft. The shaft has a distal working end configured for insertion through an incision in a body wall into a body cavity of a patient. The remote center manipulator comprises an articulate linkage assembly having a mounting base rotationally coupled to a parallelogram linkage base for rotation about a first axis. The parallelogram linkage base is coupled to the instrument holder by a plurality of links and pivots. The links and pivots define a parallelogram so as to constrain the elongate shaft of the instrument relative to a center of rotation when the instrument is mounted to the instrument holder and the shaft is moved along a plane of the parallelogram. The first axis and the parallelogram intersect the shaft at the center of rotation. Significantly, the parallelogram is angularly offset from the first axis. For example, a distal end of the parallelogram extending from a joint adjacent the instrument holder to the center of rotation is angularly offset from the elongate shaft.

In still another aspect of the present invention, a remote center manipulator for pivotal motion of a surgical instrument is provided. The surgical instrument coupleable to an instrument holder during minimally invasive robotic surgery includes an elongate shaft. The shaft has a proximal end and a distal working end configured for insertion through an incision in a body wall into a body cavity of a patient. The remote center manipulator comprises a linkage base, a first linkage assembly, and a second linkage assembly. The first linkage assembly is pivotally supported by the linkage base and has a first outer housing. The second linkage assembly is cantilevered between a proximal pivotal joint and a distal pivotal joint and defines a second linkage assembly axis therebetween. The proximal pivotal joint couples the second linkage assembly to the first linkage assembly. The distal pivotal joint couples the second linkage assembly to the instrument holder. The first and second linkage assemblies constrain lateral motion of the shaft to pivotal motion about a center of rotation disposed along the shaft. The second linkage has a second outer housing having a recess disposed between and separated from the first joint and the second joint so that the first outer housing of the first linkage assembly can protrude into the recess and across the second linkage axis when the proximal end of the shaft moves toward the linkage base. The second linkage assembly may comprise a flexible member in tension between the proximal pivotal joint and the distal pivotal joint, and at least one guide engaging the flexible member laterally so as to displace the flexible member away from the recess.

In still another aspect of the present invention, a method for performing minimally invasive robotic surgery within a body cavity of a patient employing a surgical instrument is provided. The surgical instrument coupleable to an instrument holder during minimally invasive robotic surgery includes an elongate shaft. The shaft has a distal working end configured for insertion through an incision in a body wall into a body cavity of a patient. The method comprises providing an offset articulate linkage assembly as described above. At least the distal working end of the instrument shaft is introduced through the incision into the body cavity. At least the shaft of the instrument is pivotally moved in at least one degree of freedom while at least a portion of the distal working end is within the body cavity. The offset articulate linkage assembly constrains lateral motion of the shaft to pivotal motion about the center of rotation so that the shaft is maintained substantially aligned through the center of rotation.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

DETAILED DESCRIPTION OF THE INVENTION

Figure 1:
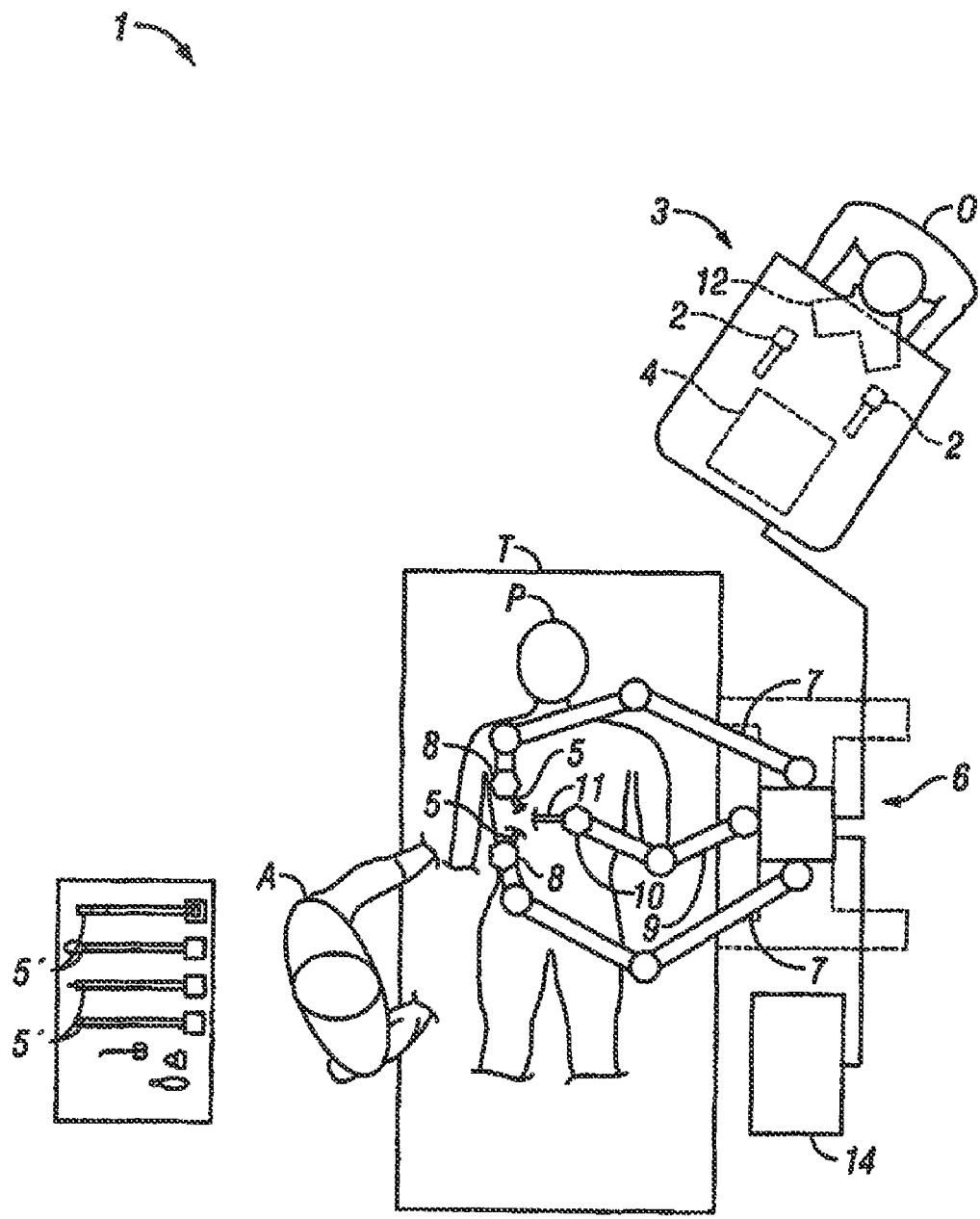
FIG. 1 is a schematic plane view of a portion of an operating theater illustrating a robotic surgical system, including a master surgeon console or workstation for inputting a surgical procedure and a robotic patient side cart for robotically moving surgical instruments having surgical end effectors at a surgical site.

FIGS. 1 through 4 illustrate a robotic surgical system 1 for performing minimally invasive robotic surgery, which is described in more detail in U.S. Pat. No. 6,246,200. An operator O (generally a surgeon) performs a minimally invasive surgical procedure on patient P lying on operating table T, the operator O manipulating one or more input devices or masters 2 at a surgeon's console 3. In response to the surgeon's inputs, a computer processor 4 of console 3 directs movement of endoscopic surgical instruments or tools 5, effecting servo-mechanical movement of the instruments via a robotic patient-side system 6 (a cart-mounted system in this example).

Typically, patient side system or cart 6 includes at least three robotic manipulator arms. Two arms or linkages 7 (mounted at the sides of cart 6 in this example) support and position servo-manipulators 8 which drive surgical tools 5; and one arm or linkage 9 (mounted at the center of cart 6 in this example) supports and positions servo-manipulator 10 which controls the motion of an endoscope/camera probe 11, which captures an image (preferably stereoscopic) of the internal surgical site.

The image of the internal surgical site is shown to surgeon or operator O by a stereoscopic display viewer 12 in surgeon's console 3, and is simultaneously shown to assistant A by an assistant's display 14. Assistant A assists in pre-positioning the manipulator 8 and 10 relative to patient P using set-up linkage arms 7, 9, in swapping tools 5 in one or more of surgical manipulator 8 (and/or 10) for alternative surgical tools or instruments 5', in operating related non-robotic medical instruments and equipment, and the like.

In general terms, the arms or linkages 7, 9 comprise a positioning linkage or set-up arm portion of patient-side system 6, typically remaining in a fixed configuration while tissue is manipulated, and the manipulators 8, 10 comprise a driven portion which is actively articulated under the direction of surgeon's console 3. The actively driven portion is herein generally referred to as a "manipulator", and the fixable portion of the positioning linkage of patient-side system linkage is referred to herein as a "set-up arm", it being noted that such set-up arms may optionally have powered and computer controlled joints.

For convenience in terminology, a manipulator such as 8 actuating tissue affecting surgical tools is generally referred to herein as a PSM (patient-side manipulator), and a manipulator such as 10 controlling an image capture or data acquisition device, such as endoscope 11, is generally referred to herein as a ECM (endoscope-camera manipulator), it being noted that such telesurgical robotic manipulators may optionally actuate, maneuver and control a wide variety of instruments, tools and devices useful in surgery.

Figure 2:
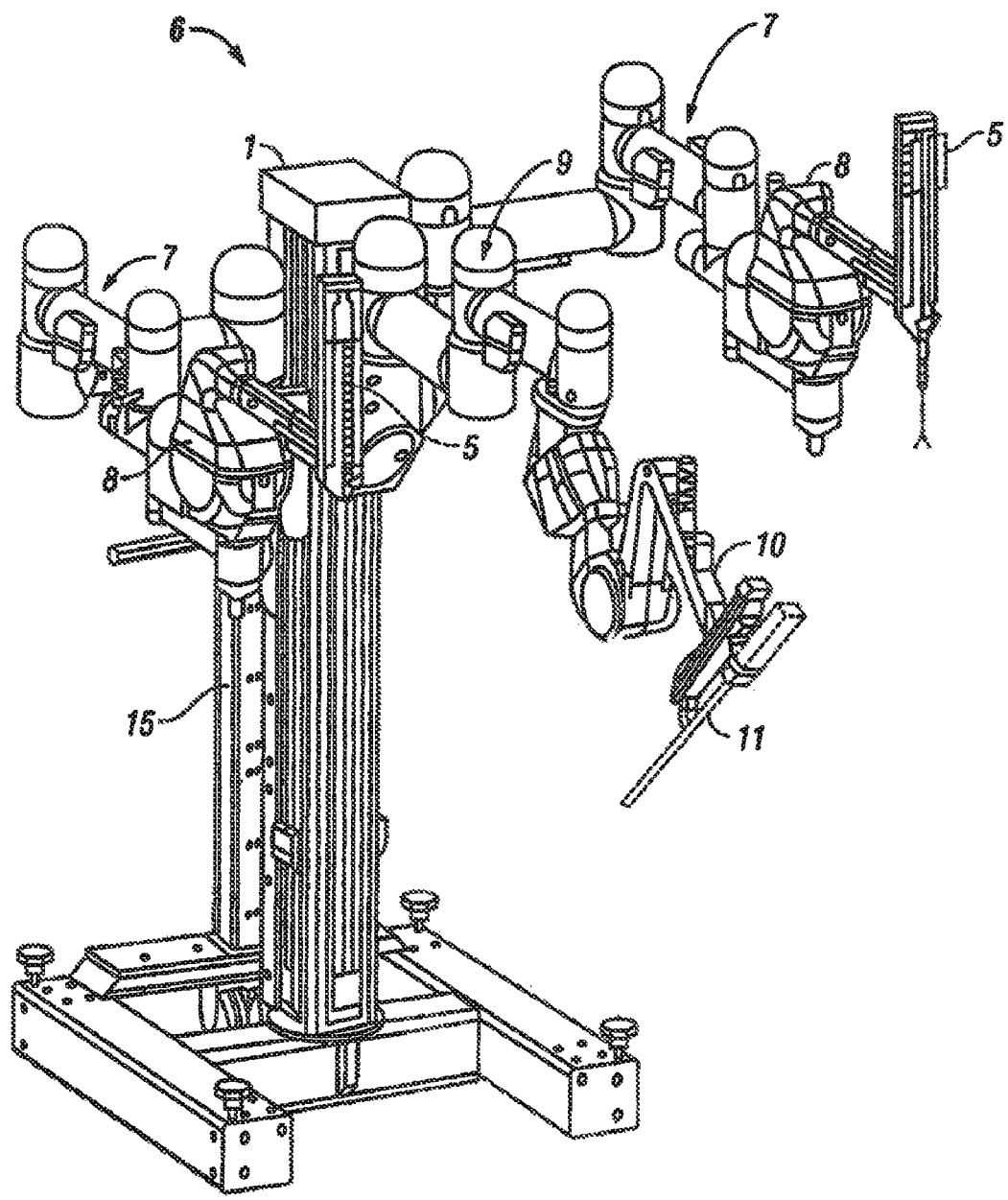
FIG. 2 is a perspective view of the robotic patient side cart or stand, including two patient side robotic manipulators and one endoscope/camera robotic manipulator.

FIG. 2 illustrates a perspective view of the cart mounted telesurgical patient-side system 6 of FIG. 1, including two PSM's 8 and one ECM 10. Cart system 6 includes a column 15 which in turn mounts three positioning linkages or set-up arms, including two PSM set-up arms 7, each supporting one of the PSM's 8, and one ECM set-up arm 9 supporting ECM 10. The PSM set-up arms 7 each have six degrees of freedom, and are mounted one on each side of centrally mounted ECM set-up arm 9. The ECM set-up arm 9 shown has less than six degrees of freedom, and ECM 10 may not include all of the tool actuation drive system provided for articulated surgical instruments, such as are typically included in PSM 8. Each PSM 8 releasably mounts surgical tool 5 (shown in dashed lines) and ECM 10 releasably mounts endoscope probe 11 (shown in dashed lines).

Figure 3B:
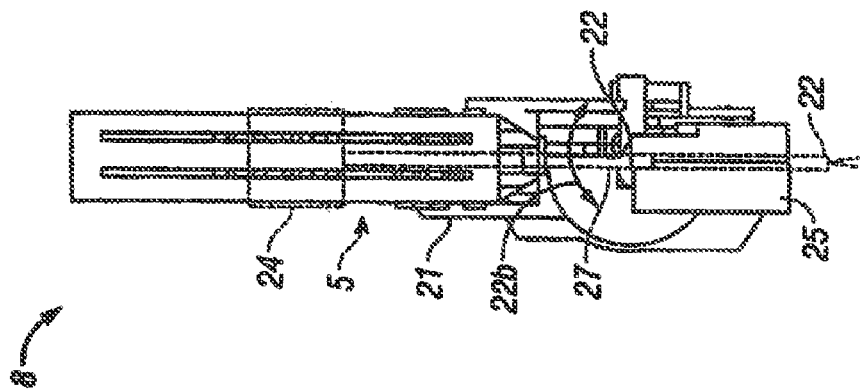
FIGS. 3A and 3B are side and front views, respectively, of the linkage of the robotic manipulators of FIG. 2.
Figure 3A:
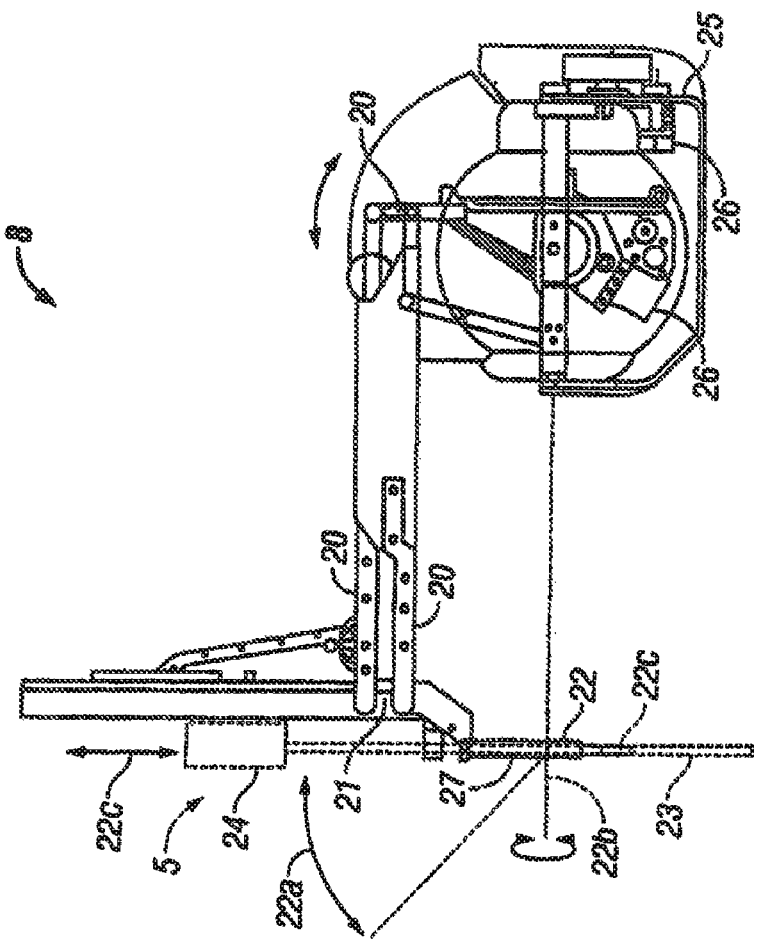

FIGS. 3A and 3B are side and front views, respectively, of the linkage of the robotic surgical manipulator or PSM 8 of FIG. 2, having a remote center mechanism. PSM 8 is one prior art example of a manipulator which may be mounted and supported by a cart mount 6, ceiling mount, or floor/pedestal mount. In this example, the PSM 8 preferably includes a linkage arrangement 20 that constrains movement of tool interface housing 21 and mounted instrument or tool 5. More specifically, linkage 20 includes rigid links coupled together by rotational joints in a parallelogram arrangement so that housing 21 and tool 5 rotate around a point in space 22, as more fully described in issued U.S. Pat. No. 6,758,843.

The parallelogram arrangement of linkage 20 constrains rotation to pivoting, as indicated by arrow 22a in FIG. 3A, about an axis, sometimes called the pitch axis, which is perpendicular to the page in that illustration and which passes through pivot point 22. The links supporting the parallelogram linkage are pivotally mounted to set-up joints (7 in FIG. 2) so that tool 5 further rotates about an axis 22b (FIG. 3B), sometimes called the yaw axis. The pitch and yaw axes intersect at the remote center 22, which is aligned along a shaft 23 of tool 5. Tool 5 has still further driven degrees of freedom as supported by manipulator 8, including sliding motion of the tool along insertion axis 22c. Tool 5 includes proximal housing 24 which mounts to manipulator interface housing 21. Interface housing 21 both provides for motion of the tool 5 along axis 22c and serves to transfer actuator inputs to tool 5 from the end effector actuator servo-mechanisms of PSM 8. In this example of a remote center system, the parallelogram arrangement 20 is coupled to tool 5 so as to mechanically constrain the tool shaft 23 to rotation about pivot point 22 as the servomechanism actuates tool motion according to the surgeon's control inputs.

As tool 5 slides along axis 22c relative to manipulator 8, remote center 22 remains fixed relative to mounting base 25 (mounting point to setup arm 7) of manipulator 8. Hence, the entire manipulator 8 is generally moved to reposition remote center 22. Linkage 20 of manipulator 8 is driven by a series of motors 26 (FIG. 3A). These motors actively move linkage 20 in response to commands from a processor (4 in FIG. 1). Motors 26 are further coupled to tool 5 so as to rotate the tool about axis 22c, and may articulate a wrist (29 in FIG. 4) at the distal end of the tool 5 about at least one, and often two, degrees of freedom. Additionally, motors 26 can be used to actuate an articulatable end effector of the tool for grasping tissues in the jaws of a forceps or the like. Motors 26 may be coupled to at least some of the joints of tool 5 using cables, as more fully described in U.S. Pat. No. 5,792,135, the full disclosure of which is also incorporated herein by reference. As described in that reference, the manipulator 8 will often include flexible members for transferring motion from the drive components to the surgical tool 5. For endoscopic procedures, manipulator 8 will often include a cannula 27. Cannula 27, which may be releasably coupled to manipulator 8, supports tool 5, preferably allowing the tool to rotate and move axially through the central bore of the cannula 27.

Figure 4:
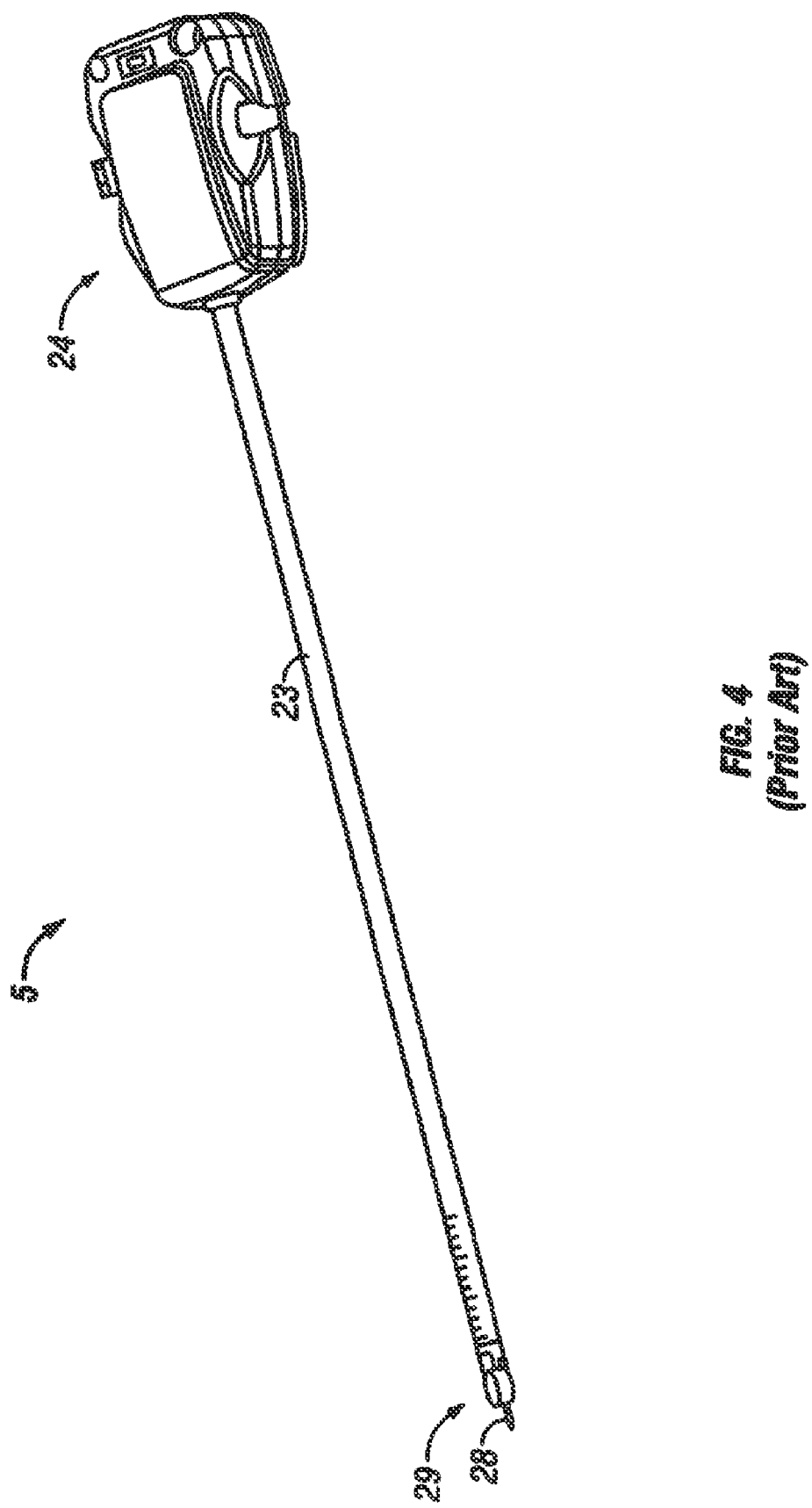
FIG. 4 is a perspective view of an articulated surgical instrument for use in the system of FIG. 1.

FIG. 4 illustrates an exploded perspective view of the articulated surgical tool or instrument 5 and proximal housing 24, that may be employed in the system of FIG. 1. Tool 5 includes elongate shaft 23 supporting end effector 28 relative to proximal housing 24. Proximal housing 24 is adapted for releasably mounting and interfacing instrument 5 to a manipulator (e.g., PSM 8 in FIGS. 1, 2, 3A, and 3B), and for transmitting drive signals and/or motion between the manipulator 8 and end effector 28. An articulated wrist mechanism 29 may provide two degrees of freedom of motion between end effector 28 and shaft 23, and the shaft 23 may be rotatable relative to proximal housing 24 so as to provide the end effector 28 with three substantially orientational degrees of freedom within the patient's body.

Figure 5B:
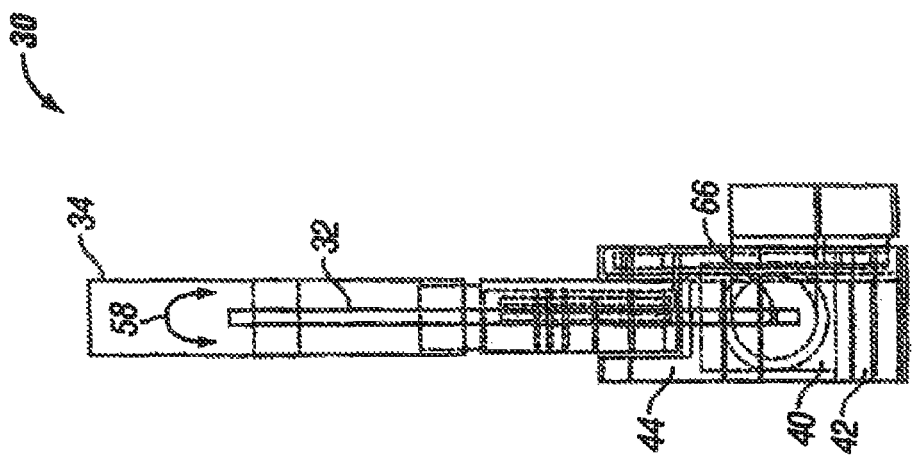
FIGS. 5A and 5B are side and front views, respectively, of an exemplary robotic manipulator linkage assembly constructed in accordance with the principles of the present invention.
Figure 5A:
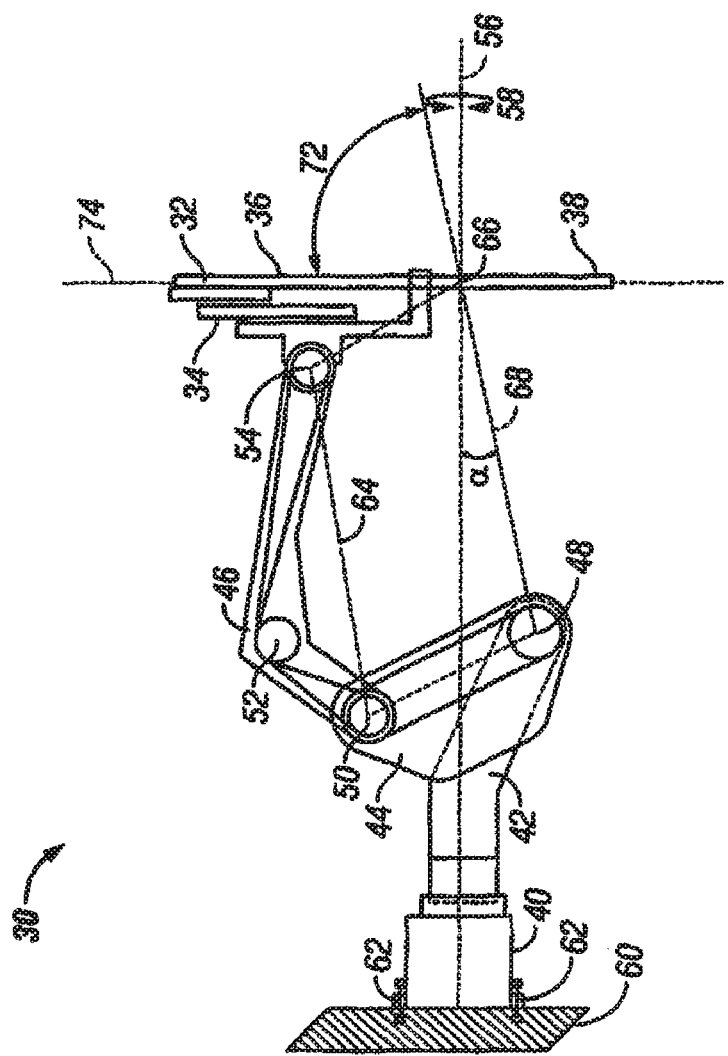

Referring now to FIGS. 5A and 5B, side and front views are illustrated of an exemplary offset remote center robotic manipulator 30 constructed in accordance with the principles of the present invention. As described in greater detail below, the refined manipulator 30 provides an offset remote center parallelogram manipulator linkage assembly which constrains a position of a surgical instrument 32 coupled to an instrument holder 34 during minimally invasive robotic surgery. The surgical instrument 32 includes an elongate shaft 36 having a distal working end 38 configured for insertion through an incision in a body wall into a body cavity of a patient. It will be appreciated that the above depictions are for illustrative purposes only and do not necessarily reflect the actual shape, size, or dimensions of the robotic surgical manipulator 30. This applies to all depictions hereinafter.

Generally, the offset remote center robotic manipulator 30 is configured to constrain shaft 36 motion relative to a center of rotation 66. As such, the shaft 36 is maintained substantially aligned through the center of rotation 66 as the shaft 36 is pivotally moved in at least one degree of freedom. Preferably, the center of rotation 66 is aligned with the incision point to the internal surgical site, for example, with a trocar or cannula at an abdominal wall during laparoscopic surgery. As such, an end effector of the surgical instrument 32 can be positioned safely by moving the proximal end of the shaft 36 using the offset remote center robotic manipulator 30 without imposing dangerous forces against the abdominal wall.

Referring back to FIG. 5A, the refined remote center manipulator generally includes an articulate linkage assembly 30 having a mounting base 40, a parallelogram linkage base 42, and a plurality of links 44, 46 and joints 48, 50, 52, 54. The term "joint" is used interchangeably with the term "pivot" herein. The mounting base 40 is rotationally coupled to the parallelogram linkage base 42 for rotation about a first axis 56, also known as the yaw axis, as indicated by arrow 58. The mounting base 40 allows for the surgical manipulator 30 to be mounted and supported by set-up arms/joints of a cart mount, ceiling mount, floor/pedestal mount, or other mounting surface. The mounting base 40 in this embodiment is fixed to base support 60 by screws or bolts 62, wherein the base support 60 is adapted to be attached to the set-up arms/joints. The parallelogram linkage base 42 is coupled to the instrument holder 34 by rigid links 44, 46 coupled together by rotational pivot joints 48, 50, 52, 54. The links 44, 46 and joints 48, 50, 52, 54 define a parallelogram 64 so as to constrain the elongate shaft 36 of the instrument 32 relative to the center of rotation 66 when the instrument 32 is mounted to the instrument holder 34 and the shaft 36 is moved along a plane of the parallelogram 64.

Significantly, the first axis 56 and the parallelogram 64 intersect the shaft 36 at the center of rotation 66, wherein the parallelogram 64 is angularly offset from the first axis 56. Specifically, a first side 68 which originates from the first pivot 48 of the parallelogram 64 adjacent the parallelogram linkage base 40 and the first axis 56 intersect the shaft 36 at the center of rotation 66, wherein the first side 68 and the first pivot 48 of the parallelogram 64 are angularly offset from the first axis 56. The first side 68 and first pivot 48 of the parallelogram 64 are offset from the first axis 56 by an angle α of at least 2 degrees, preferably by 10 degrees. Generally, the first side 68 and first pivot 48 of the parallelogram 64 are offset from the first axis 56 by angle α in a range from about 2 degrees to about 45 degrees, preferably in a range from about 2 degrees to about 35 degrees.

Figure 6A:
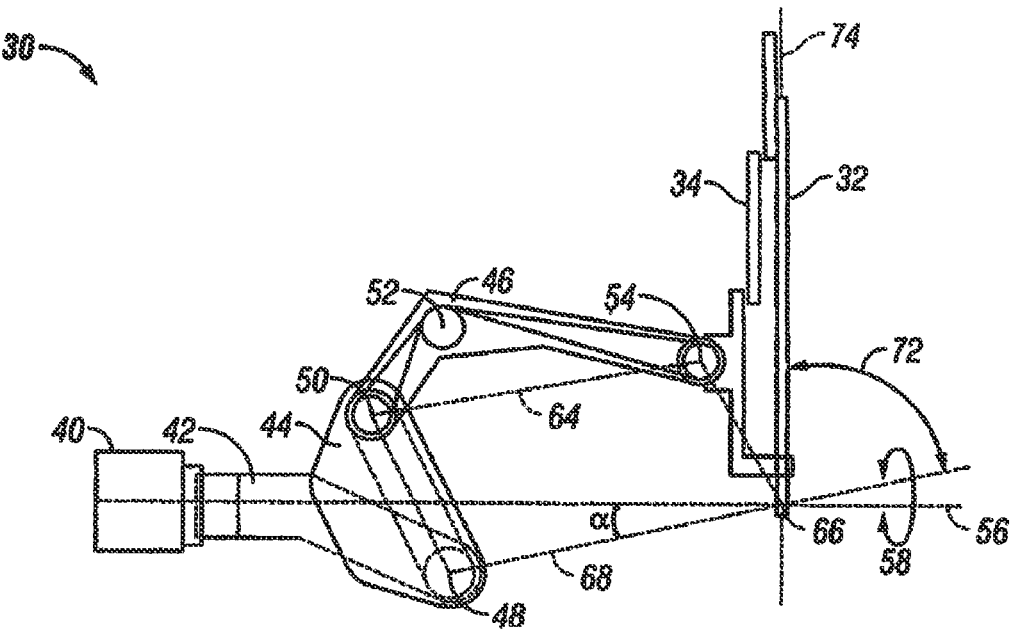
FIGS. 6A and 6B are additional side views of the exemplary robotic manipulator linkage assembly.
Figure 6B:
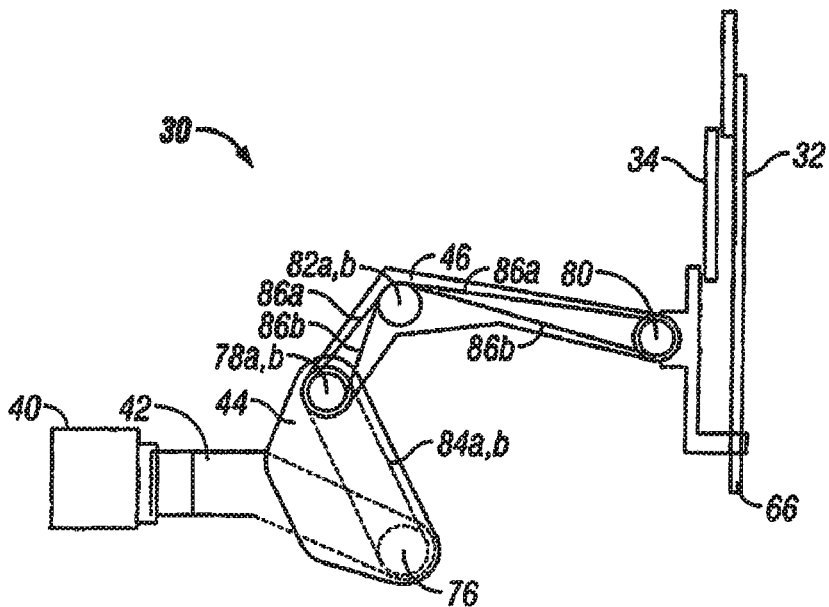
Figure 7A:
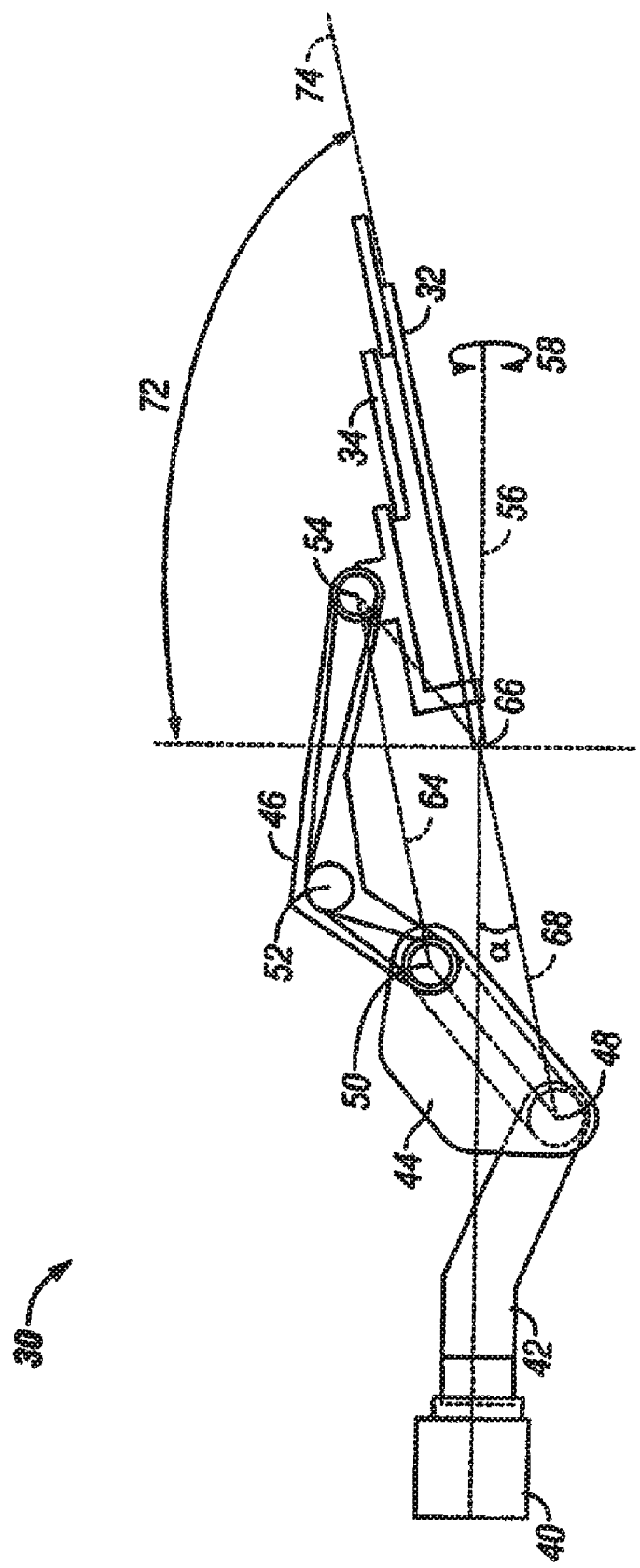
FIGS. 7A and 7B are side views of the exemplary robotic manipulator linkage assembly illustrating an improved range of motion along a pitch axis.
Figure 7B:
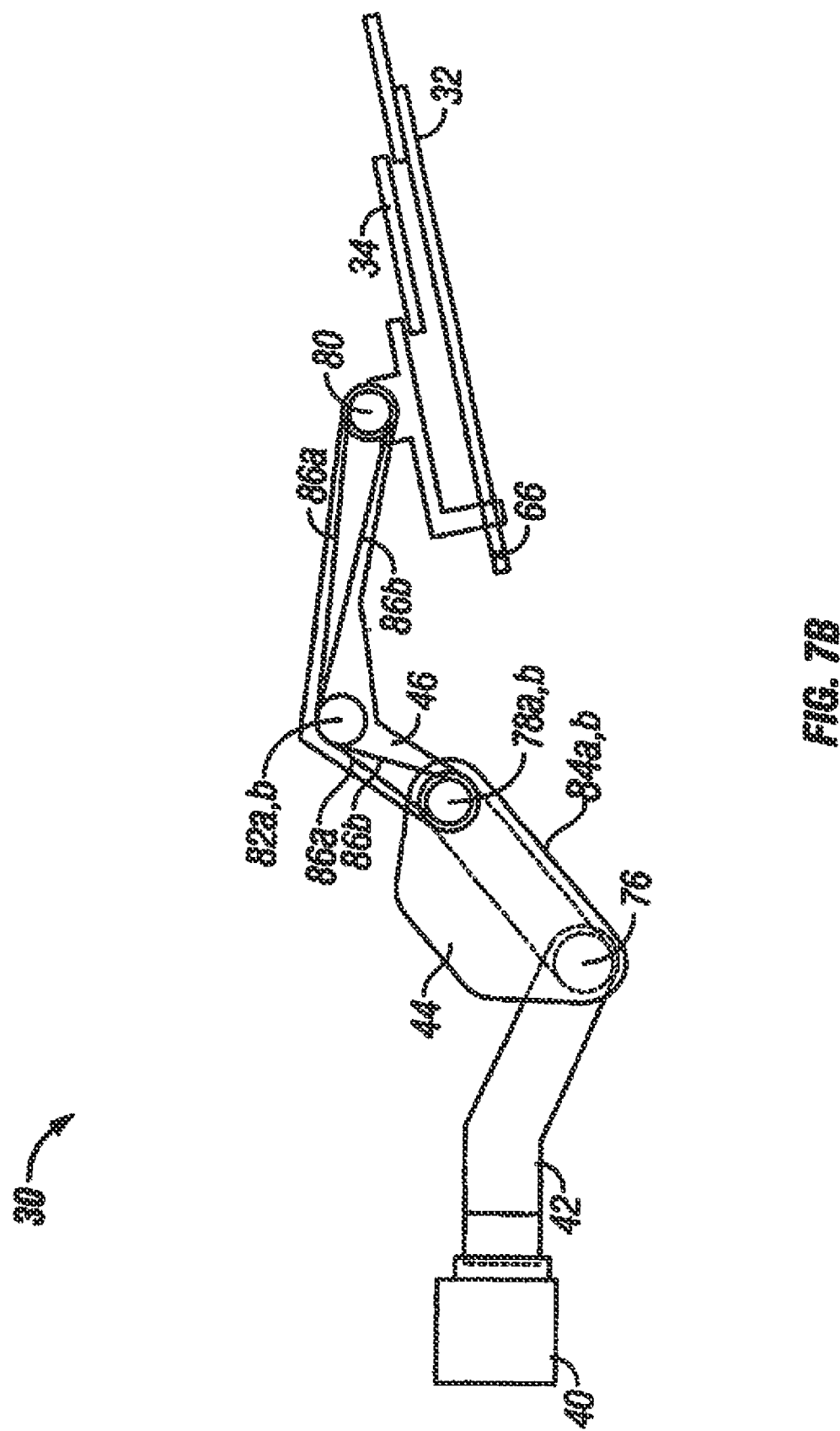

Referring now to FIGS. 6A and 6B, additional side views of the exemplary robotic manipulator linkage assembly 30 are illustrated showing the instrument holder 34 in an extended position. The offset parallelogram 64 arrangement allows for improved rotation of instrument 32 and holder 34 over the prior art example described in FIGS. 3A and 3B while the remote center of rotation 66 remains at the same location. Specifically, as shown in FIGS. 7A, 7B, 8A, 8B, 9C and 9D, the offset articulate linkage assembly 30 provides an improved range of shaft 36 motion that is greater than ±55 degrees relative to a second axis (which is perpendicular to the page in these illustrations and which passes through pivot point 66), preferably greater than ±60 degrees relative to the second axis. Generally, the offset articulate linkage assembly 30 constrains shaft 36 motion about pivot point 66 in a range from ±75 degrees relative to the second axis as indicated by arrow 72, wherein the second axis is sometimes referred to as a pitch axis. The manipulator 30 also provides an improved range of shaft 36 motion that is greater than ±90 degrees relative to the first axis 56, preferably greater than ±95 degrees relative to the first axis 56, as indicated by arrow 58 in FIGS. 9A and 9B. Typically, the cantilevered parallelogram linkage base 42 constrains shaft 36 motion about pivot point 66 in a range from ±168 degrees relative to the first axis 56.

Additionally, similar to the discussed prior art, the yaw axis 56, the pitch axis (which is perpendicular to the page), and an insertion axis 74 all intersect with each other at the remote center 66, which is aligned along a shaft 36 of the instrument 32. Thus, the instrument 32 can be pivotally rotated though desired angles as indicated by arrows 58 and 72 while the remote center of rotation 66 remains fixed in space relative to the mounting base 40 (mounting point to set-up arm) of manipulator 30. Hence, the entire manipulator 30 is generally moved to re-position the remote center 66. It will further be appreciated that the instrument 32 still has further driven degrees of freedom as supported by the offset remote center manipulator 30, including sliding motion of the instrument along the insertion axis 74.

The new and improved offset articulate linkage assembly 30 which decouples the first pivot 48 and first side 68 of the parallelogram 64 from the yaw axis 56 advantageously enhances the range of instrument 32 motion about pivot point 66 relative to the second axis, as indicated by arrow 72. The manipulator 30 further allows for an enhanced range of motion relative to the first axis 56, as indicated by arrow 58. An improved pivot range of motion along pitch and yaw axes in turn enhances the efficiency and ease of use of such robotic surgical systems. For example, the overall complexity of the robotic surgical system may be reduced due to the improved range of motion of the system. Specifically, the number of degrees of freedom in the set-up joints/arms may be reduced (e.g., less than six degrees of freedom). This allows for a simpler system platform requiring less pre-configuration of the set-up joints. As such, normal operating room personnel may rapidly arrange and prepare the robotic system for surgery with little or no specialized training.

Figure 8A:
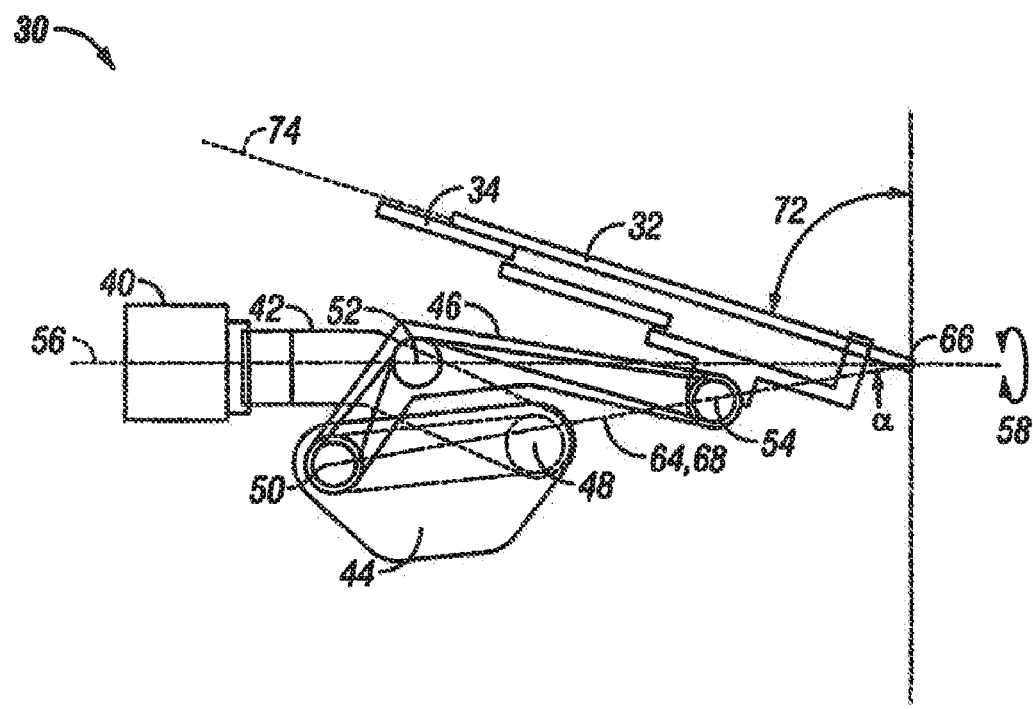
FIGS. 8A and 8B are side views of the exemplary robotic manipulator linkage assembly illustrating an improved range of motion along a pitch axis.
Figure 8B:
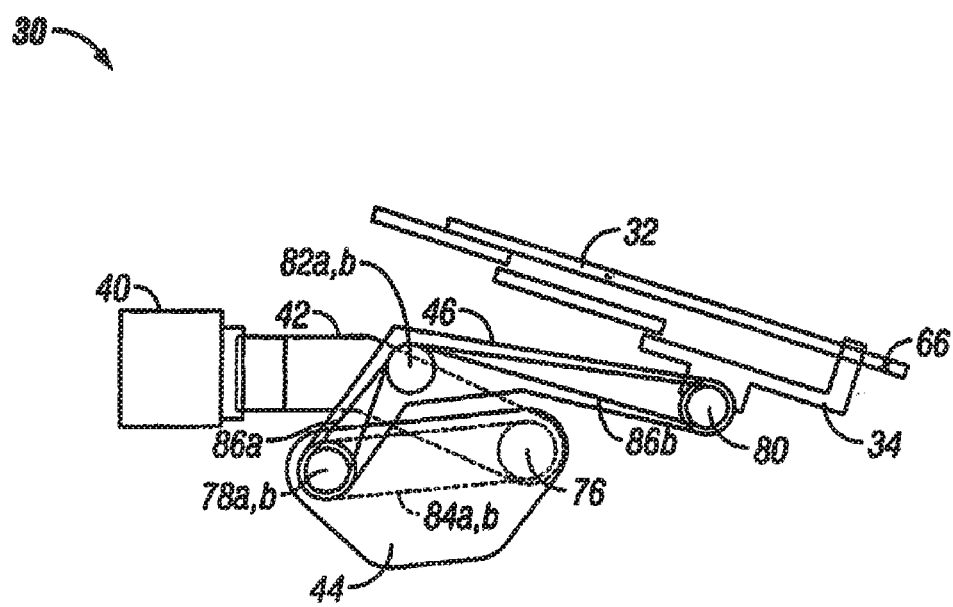
Figure 9A:
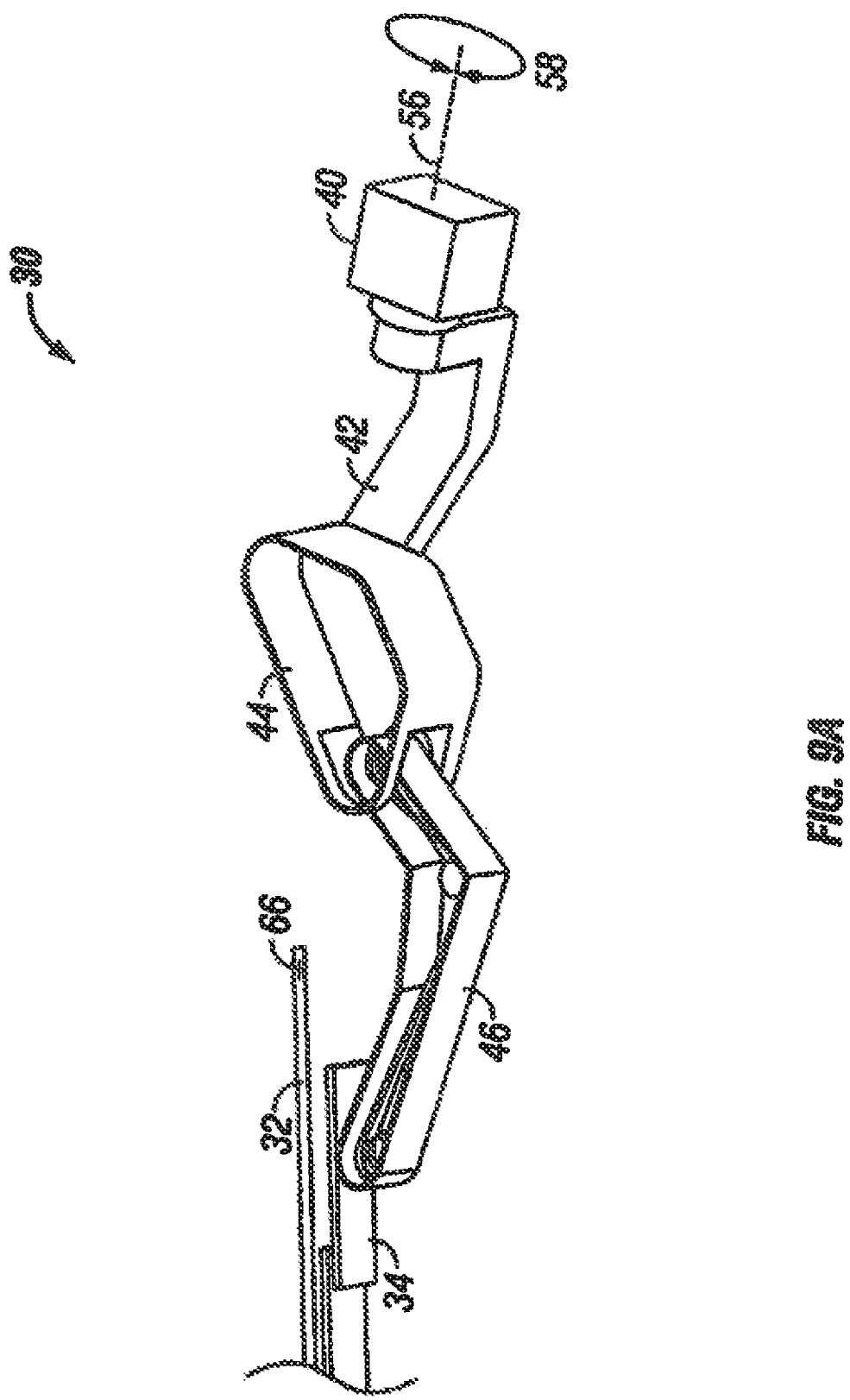
FIGS. 9A through 9D are perspective view of the exemplary robotic assembly manipulator linkage illustrating an improved range of motion along both the pitch and yaw axes.
Figure 9B:
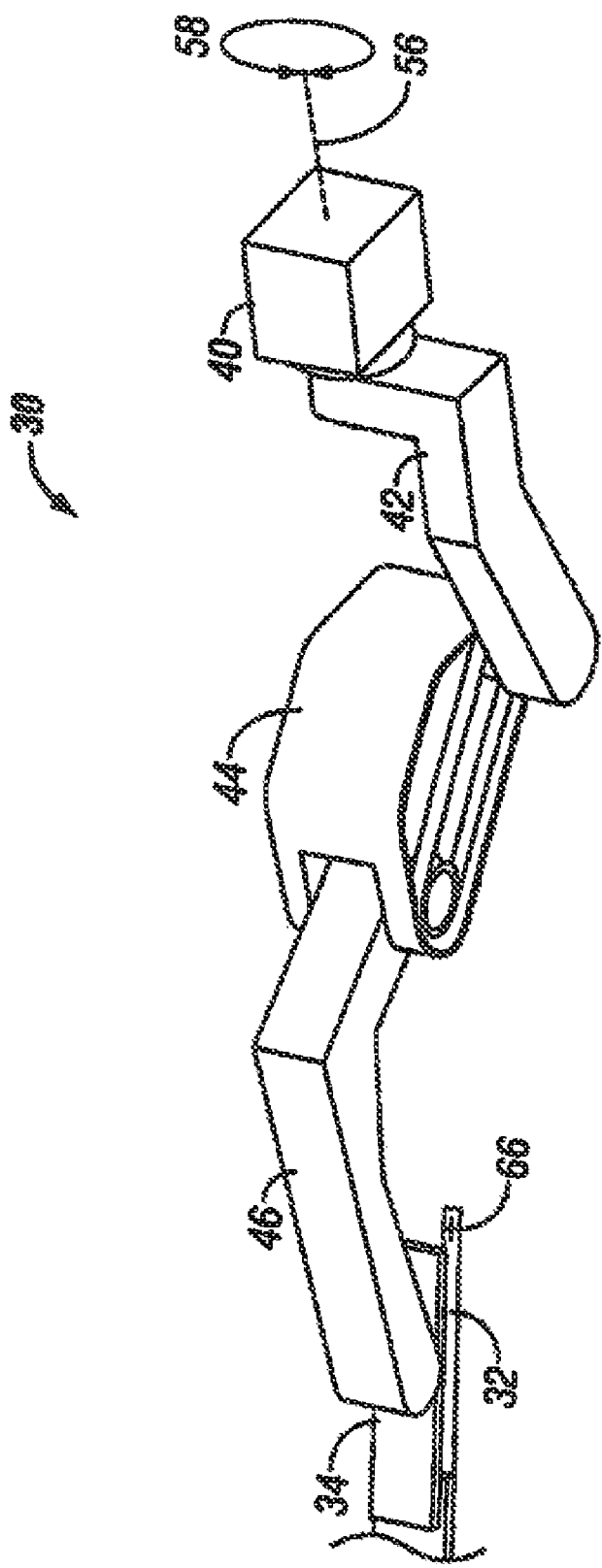
Figure 9C:
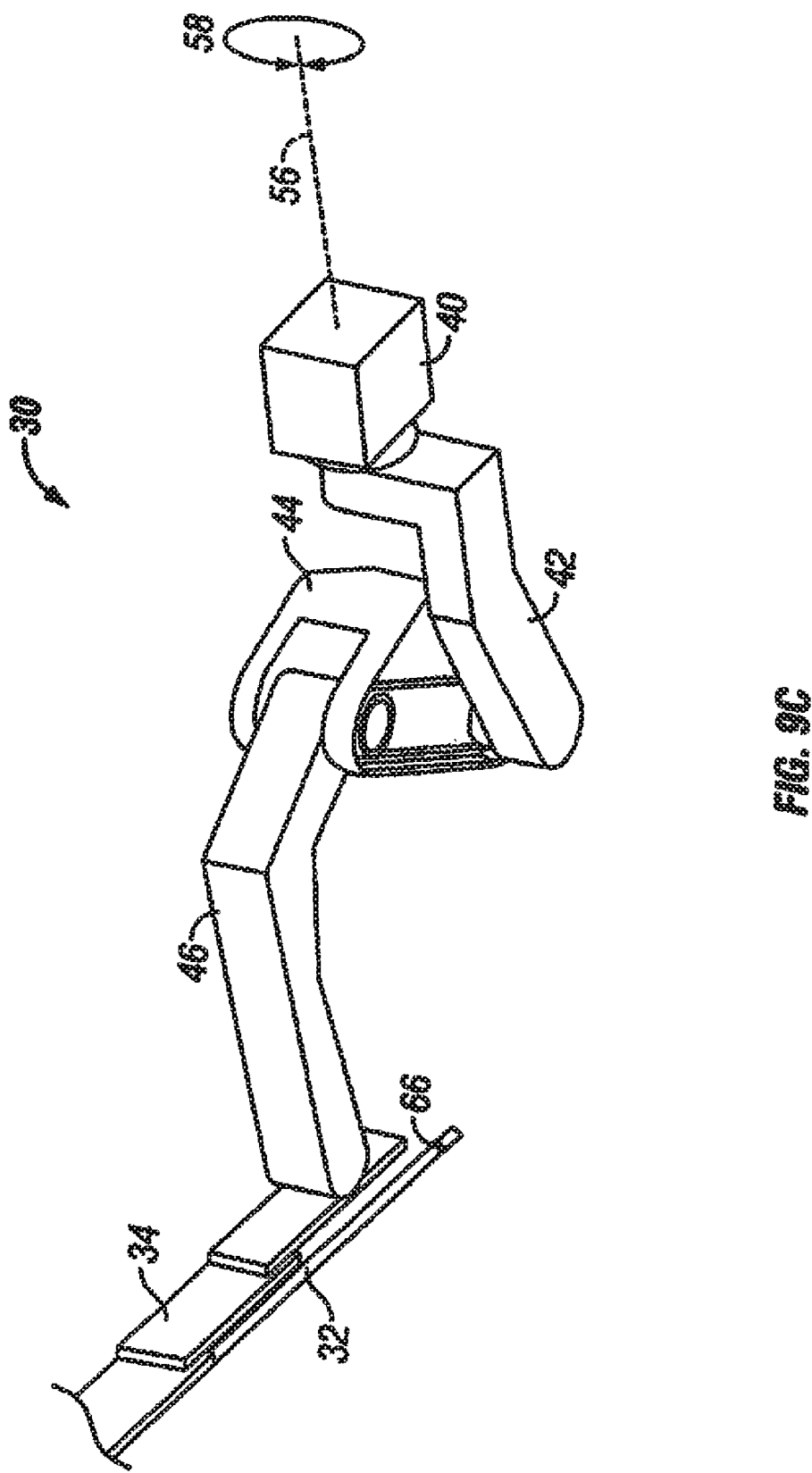
Figure 9D:
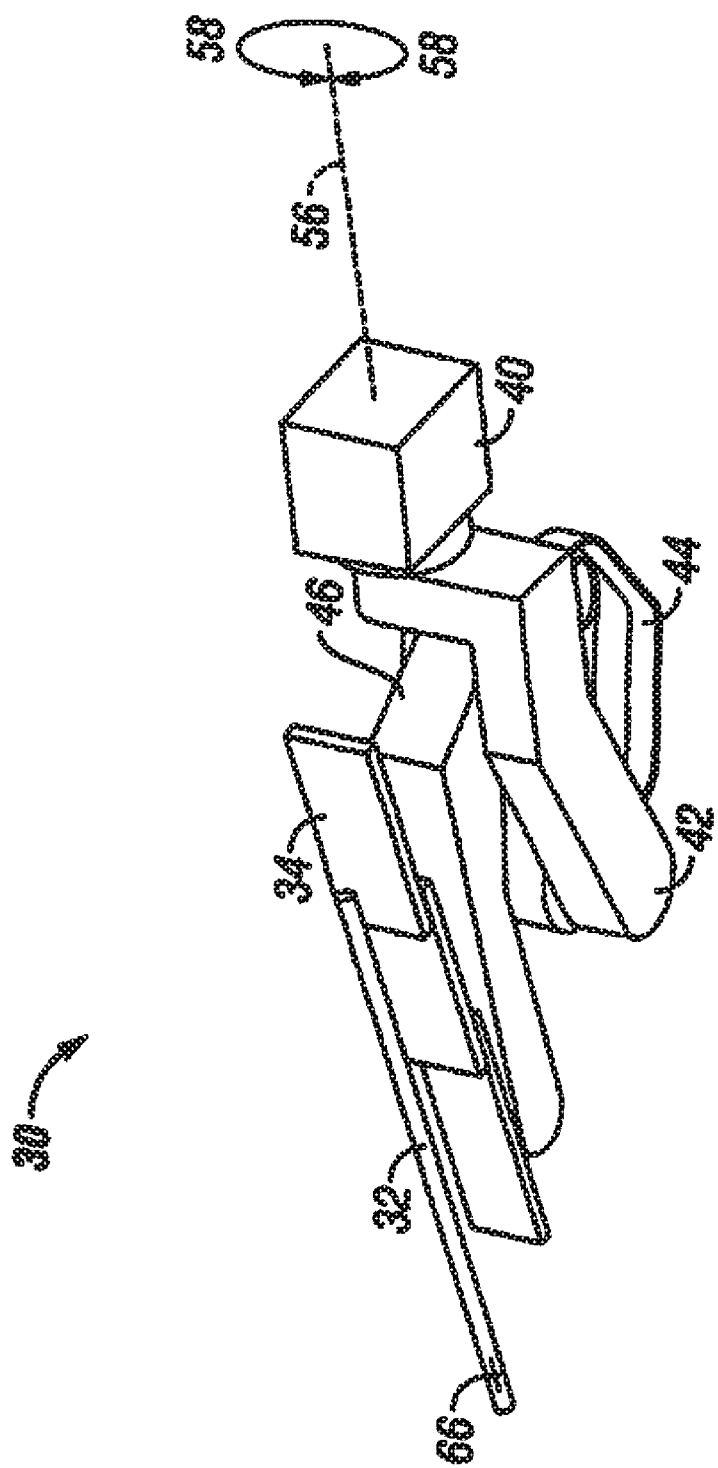

The plurality of links comprise an offset yaw link 42, a lowered vertical link 44, and a main bent link 46. The main link 46 is bent at an angle so as to provide clearance for the vertical link 44 to rest on the main bent link 46. This clearance prevents inter-linkage collisions between the vertical link 44 and the main bent link 46. For example, the main link 46 may be bent at an angle of about 22 degrees to allow clearance over a pitch dive 72 as shown in FIGS. 8A, 8B, and 9D. In such an embodiment, the main bent link 46 and the vertical link 44 as well as the instrument holder 34 are located in the same plane. It will be appreciated however that the main link 46 and the vertical link 44 may alternatively be offset in different planes (i.e., placed side by side) to reduce inter-linkage collisions in lieu of bending main link 46. The vertical link 44 pivot 48 is lower relative to the yaw axis 56 so as to provide the offset parallelogram 64 arrangement, as discussed above. The yaw link 42 is offset from links 44, 46, as best seen in FIGS. 9B through 9D. Link 42 and links 44, 46 are not in the same plane, but are rather offset side by side so as to reduce the possibility of inter-linkage collisions between link 42 and links 44, 46.

At least one of the rigid links 42, 44, 46 coupled together by rotational pivot joints 48, 50, 52, 54 are not completely balanced in at least one degree of freedom. As such, a brake system may be coupled to the articulate linkage assembly 30. The brake system releasably inhibits articulation of at least one of the joints 48, 50, 52, 54. It will be appreciated that the offset remote center manipulator 30 may comprise a lighter system as the linkage is free of any counter-balancing weights. As such, the links 42, 44, 46 will preferably comprise sufficiently rigid and stiff structures so as to support any vibration issues associated with the lighter manipulator 30. It will further be appreciated that the offset remote center manipulator 30 may optionally be balanced by the use of weights, tension springs, gas springs, torsion springs, compression springs, air or hydraulic cylinders, torque motors, or combinations thereof.

Referring back to FIGS. 6B, 7B, and 8B, the offset remote center manipulator 30 may preferably comprise six pulleys 76, 78a, 78b, 80, 82a, 82b and four flexible elements 84a, 84b, 86a, 86b coupled to the pulleys 76, 78a, 78b, 80, 82a, 82b that are configured to constrain shaft 36 motion relative to the center of rotation 66. Links 42 and 46 are kept from rotating relative to each other by flexible elements 84a, 84b running on two pulleys 76, 78a, with one pulley 76 fixed to link 42 and one pulley 78a fixed to link 46. Links 44 and 34 are likewise kept from rotating relative to each other by a flexible elements 86a, 86b running on the remaining four pulleys 78b, 80, 82a, 82b, with one pulley 78b fixed to link 44, one pulley 80 fixed to link 34, and idler pulleys 82a, 82b to get the flexible elements 86a, 86b around the main bent link 46. Hence, links 42 and 46 can translate but not rotate relative to each other to maintain the parallelogram shape 64. Likewise, links 44 and 34 can translate but not rotate relative to each other to maintain the parallelogram shape 64. It will be appreciated that the term pulley 76, 78a, 78b, 80, 82a, 82b can include wheels, gears, sprockets, and the like.

The flexible element 84a, 84b, 86a, 86b may include belts, chains, or cables connected around the pulleys 76, 78a, 78b, 80, 82a, 82b. Preferably, the flexible elements comprise multi-layer metal belts, such as stainless steel belts having a breaking strength of approximately 800 lbs and being about a quarter inch wide. The belts are preferably multi-layered utilizing at least 3 plies, preferably 5 plies to be strong enough to carry an adequate tension load yet sufficiently thin enough to not fatigue when repeatedly bent around the pulleys. Pulleys 76 and 78a have approximately the same diameter, e.g., 2.2 inches. Smaller pulleys 78b and 80 have approximately the same diameter, e.g., 1.8 inches. There are two idler pulleys 82a, 82b at the bend of the main link 46 to facilitate running of belts 86a, 86b in opposite directions so as to allow for attachment of the belts ends to be more robust. Utilization of non-continuous offset belts 84a, 84b and 86a, 86b provides for stress reduction, particularly at the attachment points, thus minimizing failures. Further, non-continuous belts allow for convenient tension and position adjustments. It will further be appreciated that belts 84a, 84b as well as belts 86a, 86b may optionally comprise continuous single belts. Additionally, the metal belts may be lightly coupled to flat flex cables that carry electrical signals along the manipulator arm.

The offset articulate linkage assembly 30 is driven by a series of motors. Motors may be located within the plurality of links to drive the pulley and belt mechanisms. Preferably, a majority of the motors are housed in the lowered vertical link 44. In particular, the motor which drives the pitch axis 72 rotating link 44 relative to link 42 through spur gears and a harmonic drive as well as the motors that run instrument actuation cables (e.g., wrist drive cables which may be spring tensioned) may be housed in link 44. Placement of the vertical link 44, the main bent link 46, and the instrument holder 34 in the same plane is advantageous as the motors that run the actuation cables are housed in link 44. Further, having the vertical link 44, the main bent link 46, and the instrument holder 34 in the same plane allows for space minimization at the distal end of the manipulator 30, which is of significant importance when performing minimally invasive robotic surgery in a confined operating environment. The motor driving the yaw axis 58 may be housed in mounting base 40.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. An apparatus comprising:
   a mounting base;
   a parallelogram linkage base having a proximal end, a distal end, and a linkage axis coupling the proximal and distal ends, the parallelogram linkage base proximal end coupled to the mounting base, the parallelogram linkage base proximal end further rotatable relative to the mounting base about a first axis, the linkage axis and the first axis intersecting at the parallelogram linkage base proximal end;
   a first link having a proximal end and a distal end, the first link proximal end coupled to the parallelogram linkage base distal end;
   a second link having a proximal end and a distal end, the second link proximal end coupled to the first link distal end, the second link constrained from rotating relative to the parallelogram linkage base; and
   an instrument holder coupled to the second link distal end, the instrument holder constrained from rotating relative to the first link, the instrument holder configured to slide along an insertion axis.

2. The apparatus of claim 1, wherein the insertion axis intersects the first axis.

3. The apparatus of claim 1, the apparatus further comprising an instrument releasably coupleable to the instrument holder, the instrument having a longitudinal axis, the sliding of the instrument holder along the insertion axis causing the instrument to slide along the instrument longitudinal axis.

4. The apparatus of claim 1, the second link being bent at an angle.

5. The apparatus of claim 4, the second link being bent at an angle of about 22 degrees.

6. The apparatus of claim 1, the first link and the second link being offset in different planes.

7. The apparatus of claim 6, wherein the insertion axis is skew from the first axis.

8. The apparatus of claim 1, the second link constrained from rotating relative to the parallelogram linkage base by flexible elements running on pulleys attached to the second link and the parallelogram linkage base.

9. The apparatus of claim 1, the instrument holder constrained from rotating relative to the first link by flexible elements running on pulleys.

10. The apparatus of claim 1, further comprising a plurality of motors housed in the first link.

* * * * *